United States Patent [19]

LaPrade

[11] Patent Number: 5,006,108

[45] Date of Patent: Apr. 9, 1991

[54] APPARATUS FOR IONTOPHORETIC DRUG DELIVERY

[75] Inventor: Ronald E. LaPrade, Miami, Fla.

[73] Assignee: Noven Pharmaceuticals, Inc., Miami, Fla.

[21] Appl. No.: 271,600

[22] Filed: Nov. 16, 1988

[51] Int. Cl.$^5$ ............................................... A61N 1/30
[52] U.S. Cl. ..................................... 604/20; 128/798; 128/803
[58] Field of Search .................................. 604/20–21; 128/419 R, 419 D, 421–423, 783, 741, 798, 802–803

[56] References Cited

U.S. PATENT DOCUMENTS

| | | | |
|---|---|---|---|
| 4,325,367 | 4/1982 | Tapper | 604/20 |
| 4,406,658 | 9/1983 | Lattin et al. | 604/20 |
| 4,713,050 | 12/1987 | Sibalis | 604/20 |
| 4,722,726 | 2/1988 | Sanderson et al. | 128/798 X |
| 4,747,819 | 5/1988 | Phipps et al. | 604/20 |
| 4,764,164 | 8/1988 | Sasaki | 604/20 |
| 4,842,577 | 6/1989 | Konno et al. | 604/20 |

Primary Examiner—Angela D. Sykes
Attorney, Agent, or Firm—Sybil Meloy

[57] ABSTRACT

An iontophoretic device for delivery of a drug comprising a flexible, non-conductive backing; first and second conductive electrodes composed of a substantially non-ionizing material in a plane, one side of the plane which is optionally attached to the optionally flexible backing, and the other side of the plane which is adapted to be affixed to one side of a flexible and electrically conductive layer containing the drug to be delivered; a source of electrical current and a device for reversing the polarity of the two electrodes. The device can additionally include the conductive layer containing the drug to be delivered, affixed to the plane of the two electrodes. An ion exchange membrane can optionally be disposed between the two electrodes and the drug-containing layer. The device can optionally contain a pulsing device or a current varying device or both to vary the amount of current delivered from time to time or in absolute amount.

9 Claims, 4 Drawing Sheets

APPARATUS FOR IONTOPHORETIC DRUG DELIVERY

BACKGROUND OF THE INVENTION

The present invention relates to transdermal (transcutaneous) drug applicators and methods of their use, as well as to a drug-containing medium for use with such applicators, and more particularly to iontophoretic drug applicators which are electrically operated and which exhibit properties which facilitate the transcutaneous delivery or transfer of drugs, and the like.

Iontophoresis has come into increasing attention as an effective method for the topical application of drugs through the skin to exert a systemic effect.

Iontophoresis is the technique of delivering ionic, ionizable or polar drugs through a person's skin, by placing a solution or other medium containing the ions, ionizable or polar substances in contact with the skin, and applying electric current to the medium. The medium containing the ions, ionizable or polar substance may be a fluid or a solid and is in contact with a first electrode. Ions are caused to migrate from the medium through the skin or tissue by the application of electric current from the first electrode, to the medium and then to a second electrode spaced from the first electrode.

Iontophoretic devices have been designed so that one electrode is in contact with the medium containing the drug of like charge to that of the electrode, while the second electrode is in contact with a medium lacking such drug. Alternatively, the second electrode can be in contact with a different drug having a charge the same as that of the second electrode.

In addition, iontophoretic devices have been proposed containing pulsing means, namely means for effecting depolarization of the electrodes at spaced intervals, in an attempt to lower the voltage needed for the iontophoresis.

The overall size of the iontophoretic device should desirably be minimized for cost effectiveness and aesthetics, and the dosage capability maximized.

It is an object of the present invention to provide improved iontophoretic devices comprising two electrodes insulated from each other, that is minimum in size and capable of maximum drug delivery, and yet reasonable in cost.

It is a further object of the present invention to provide an improved iontophoretic system utilizing improved electrode construction, which permits delivery of a single drug through both electrodes, by use of a means to reverse the polarity of the two electrodes. The means for reversing the polarity of the two electrodes can be an electronic switching device, which can optionally be coupled to a pulse generating device. The pulse generating device permits the delivery of electrical current in pulses, which, in cooperation with the electronic switching device, can be timed to reverse the polarity of the electrodes at spaced intervals related to the pulses, or independent of the pulses. Still another object of this invention is an iontophoretic device having means to vary the amount of current delivered to the device.

Another object of this invention is the provision of a drug-containing medium for use in the iontophoretic device, which layer is backed on both sides with a pressure sensitive adhesive.

These and other objects and advantages of the invention, will become more apparent from a reading of the following detailed description of the preferred modifications and embodiments of the invention.

SUMMARY OF THE INVENTION

An iontophoretic device for delivery of a drug comprising a flexible, non-conductive backing; first and second conductive electrodes composed of a substantially non-ionizing material in a plane, one side of the plane which is optionally attached to the optionally flexible backing, and the other side of the plane which is adapted to be affixed to one side of a flexible and electrically conductive layer containing the drug to be delivered; a source of electrical current and means for reversing the polarity of the two electrodes. The device can additionally include the conductive layer containing the drug to be delivered, affixed to the plane of the two electrodes. An ion exchange membrane can optionally be disposed between the two electrodes and the drug-containing layer. The device can optionally contain pulsing means or current varying means or both to vary the amount of current delivered from time to time or in absolute amount.

DETAILED DESCRIPTION OF THE INVENTION

The present invention generally provides an iontophoretic device which comprises:

an optionally flexible, non-conductive backing;

first and second conductive electrodes in a plane, one side of which is optionally attached to a flexible backing, and composed of a substantially non-ionizing material;

an optional conductive layer containing the drug to be delivered affixed to the two electrodes in communication;

a source of electrical current;

means for reversing the polarity of the two electrodes;

an optional pulsing generator to cause the current to be delivered to the electrodes in discrete segments;

an optional current regulator to vary the voltage of the current to be delivered;

an optional ion exchange membrane carried between the electrodes and the drug-containing layer; and an optional, pressure-sensitive adhesive on each side of the drug-containing layer, to hold said layer in contact with the electrodes on one side and with the skin on the other side.

Figure 1:
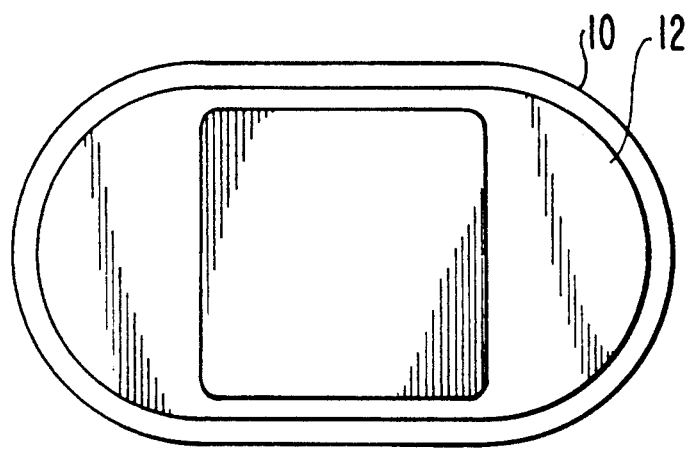
FIG. 1 is a top view of the first embodiment of the present invention.
Figure 2:
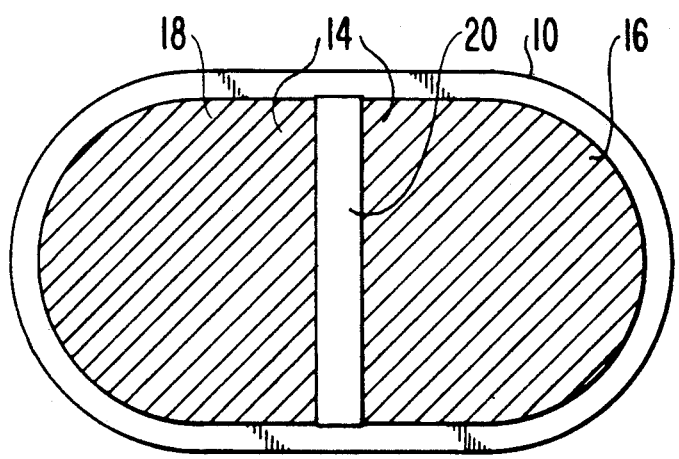
FIG. 2 is a bottom view of the invention of FIG. 1.
Figure 3:
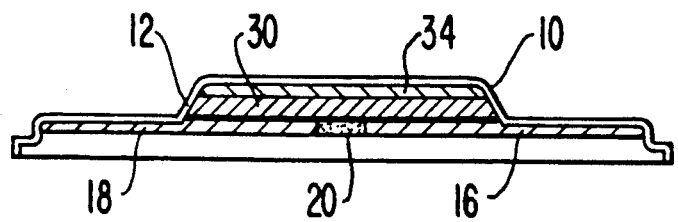
FIG. 3 is a cross-section of the invention of FIG. 1.

Referring to FIGS. 1, 2 and 3, there is shown a first embodiment of iontophoretic device 10 which comprises a non-conductive polymeric, outer-layer 12 of polyvinlychloride, or other flexible, non-conductive backing material. On the reverse side of the iontophoretic device 10, shown in FIG. 1, as shown in FIG. 2, there is a layer 14 serving as a dual electrode. Layer 14 comprises a conductive material, such as copper, silver or molybdenum metals, or other substantially non-ionizing material. Specifically, the layer 14 is composed of a material that will not cause the formation of substantial amounts of ions in competition with those of the ionized drugs, such as hydronium ions. An insulating material 20 in FIGS. 2 and 3, acts to separate layer 14 into two portions 16 and 18, which thus permits the two portions to serve as electrodes of opposite charge.

Referring to FIG. 3, a layer 30 is a thin integrated circuit containing a direct current pulse generator, a current regulator circuit and a polarity switching means (not shown in FIG. 3).

Figure 4:
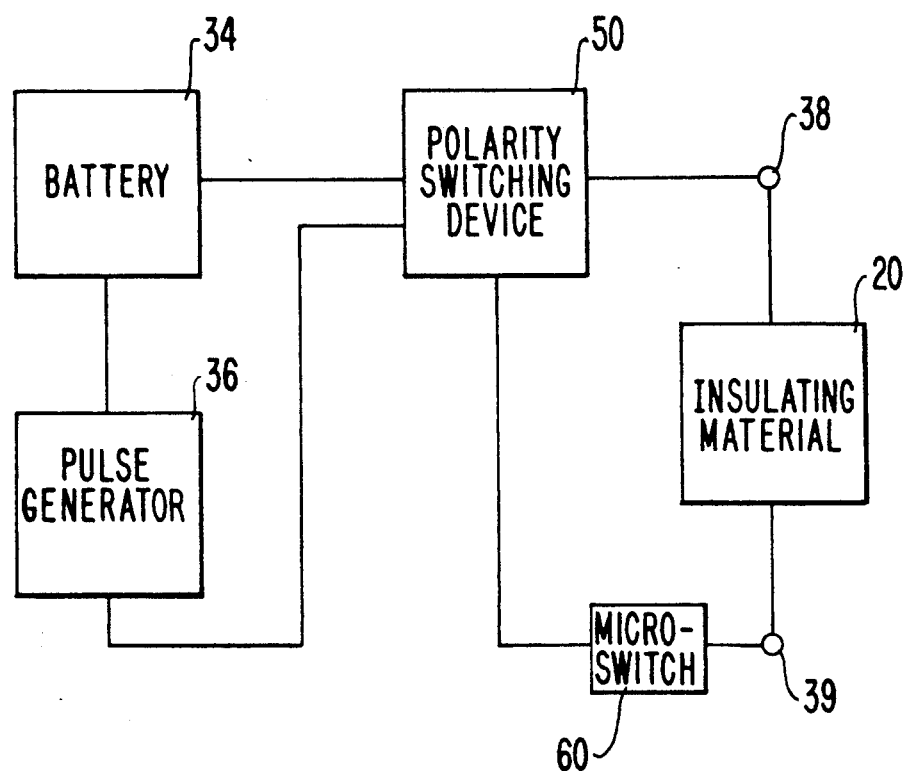
FIG. 4 is a block diagram of the electrical circuit for the device shown in FIG. 3.

FIG. 4 is a block diagram of a system used to permit pulsing and polarity switching of the device. In FIG. 4, electrical pulse-generating device 36 is connected to polarity switching device which is connected to anode 38 and cathode 39 sections of the device. The battery 34 is connected to the pulse generating device via suitable electrical conducting materials. Some suitable pulse generating devices are described in Sasaki, European Patent application No. 84305910.6, assigned to Kabushiki Kaisya Advance Kashatsu Kenkyujo, the disclosure of which is incorporated by reference.

By means of the time relay device 36, the polarity of the iontophoretic device can be changed at some number of pulses to obtain an active to indifferent electrode ratio to obtain maximum delivery of the ionized drug used.

Figure 5:
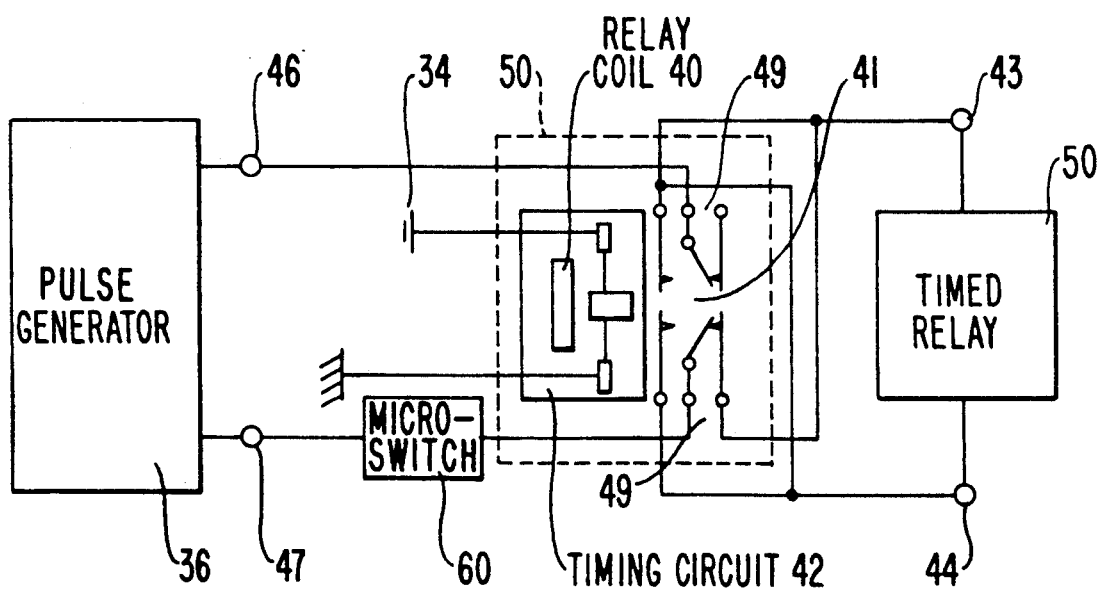
FIG. 5 is an electrical schematic drawing of the circuit of the polarity switching device used with the invention of FIG. 3.

The layer 30 of FIG. 3 can be provided with an external current generator and switching device, a schematic representation of which is shown schematically in FIG. 5. A battery 34 consists of multiple layers of conductive flexible polymers in a gel substance that will generate voltage to the pulse generating device and is electrically connected to the polarity switching device 50. The insulating material 20 shown in FIGS. 2 and 3 absorbs excess moisture from the drug layer to prevent any shorting of the two electrodes during operation.

FIG. 5 is a circuit diagram of switch means permitting reversal of the polarity of the electrodes with desired time period and consists of a time relay circuit or any other timing circuit incorporated into the total circuit of FIG. 4.

The operation of the device incorporating the circuit of FIG. 5 is as follows: A constant power source is obtained from the battery 34 and is used to power the timing circuit 42 of the timed relay 50. A microswitch 60 is provided in the device to turn on time relay 50 when drug matrix is affixed to the iontophoretic device. Relay 41 is timed via timing circuit 42, so that the relay contacts 49 change positions after the desired number of pulses. During this period, the pulsing device, pulse current at connection 46 from pulsing device 36, is in electrical contact with active electrode 43 while indifferent electrode 44 is in contact with connection 47 from pulsing device. At the end of desired number of pulses and when time relay time is zero, contacts 49 change position (power is applied to relay coil 40), so that connection 46 is now in contact with the now active electrode 44 and connection 47 is in contact with the now indifferent electrode 43. The timing circuit of timed relay 50 is reset automatically at the end of each pulsing period thereby timing up during one period and timing down during the next period. By so changing polarity of the active and indifferent electrode after each set of pulses (periods) the drug delivers in both portions of the device shown in FIG. 2 and is maintained during subsequent periods of the pulsing device.

Figure 6:
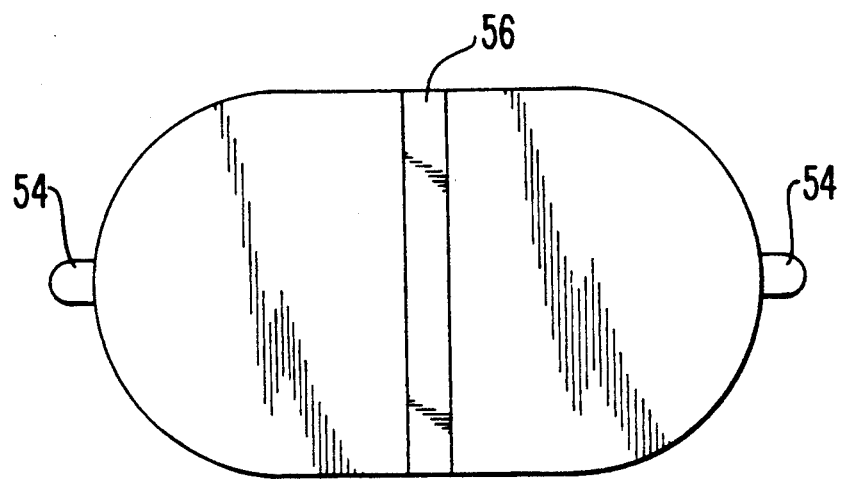
FIG. 6 is a top view of the drug-containing conductive gel layer used with the invention of FIG. 3.
Figure 7:
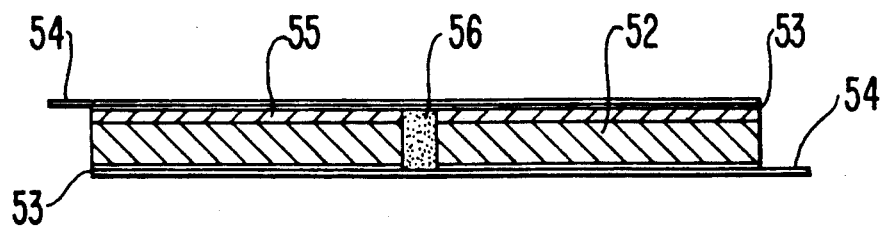
FIG. 7 is a cross-sectional view of the drug layer of FIG. 6.

A plane view and a cross-section view of the conductive gel (or other supporting conductive media), containing the drug is illustrated in FIG. 6. In the cross-section shown in FIG. 7, a conductive adhesive layer 53 is laminated to the top of ionic membrane 55. Ionic membrane 55 is laminated to the gel layer 52 containing the drug for contact with the skin. Insulator 56 separates the two equal halves of the conductive gel for contact with the two electrodes and prevents shorting the drug gel matrix to reduce current density concentrations at any spot smaller than the electrode surface area.

One conductive material for use in making a gel layer includes, for example, the resinous polysaccharide karaya gum. Other conductive materials that can be used to form a gel include tragacanth gum, polyvinyl alcohol, polyvinyl methacrylate, polyacrylic acid, polyacrylic esters. These natural and synthetic resins are combined with water or polyols, such as ethylene glycol and glycerin. Additives such as polyethylene glycol, proplylene glycol and diproplylene glycol in combination with oleic acid can be added to the gel to improve drug delivery through the skin, thus reducing the current density to deliver a given drug.

An ionized drug or conductive salts thereof are mixed with the aforementioned material making the gel more conductive for iontophoresis. Release liner 54 can be used on both sides of the gel layer to protect pressure sensitive adhesives until they are applied to the patient for drug delivery.

Figure 8:
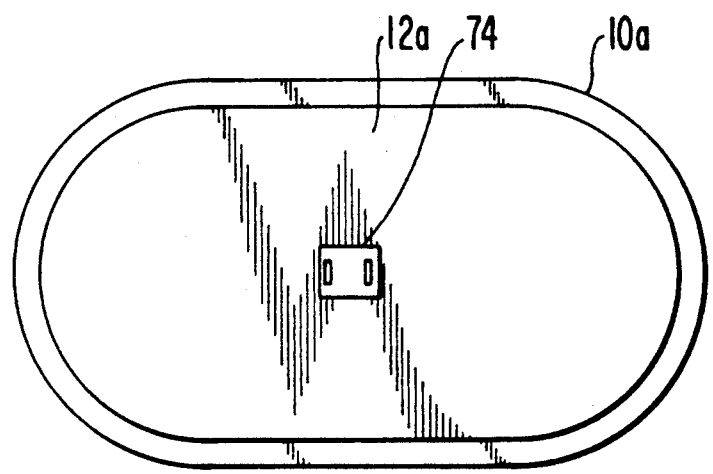
FIG. 8 is a top view of a second embodiment of the present invention.
Figure 9:
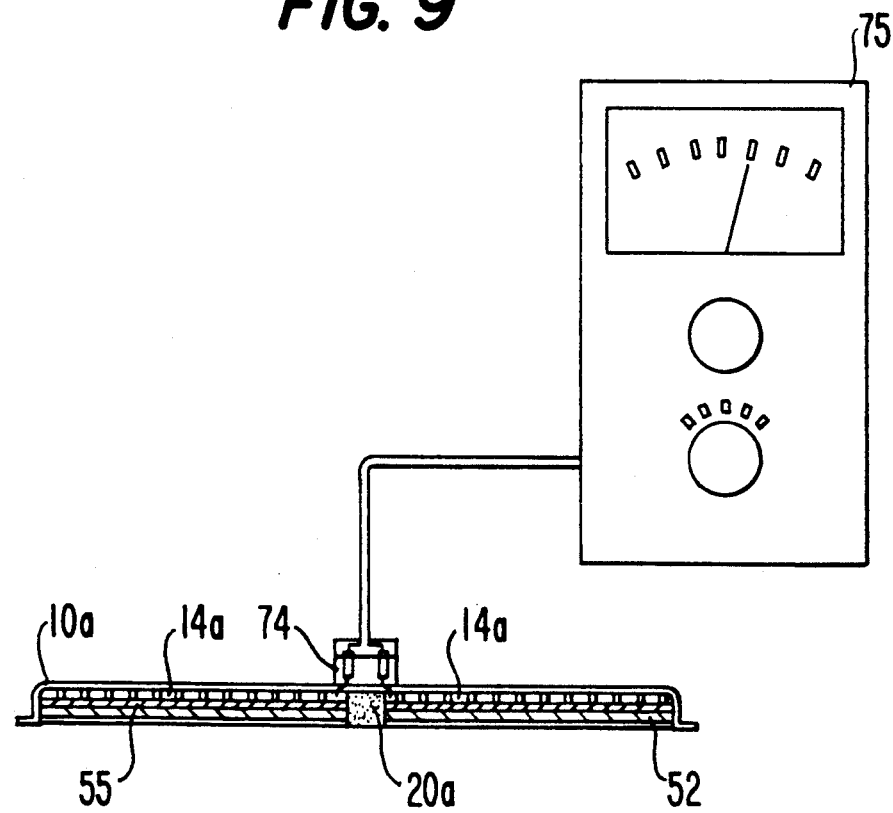
FIG. 9 is a cross-sectional view of the second embodiment of the present invention.

The device of FIGS. 8 and 9 is a second embodiment of the invention which utilizes an external power source, a pulse generating device, and a polarity reversing device for delivering higher current densities than are possible by the devices shown in FIGS. 1 to 3. In FIGS. 8 and 9 shown outer layer 10a is a polymeric non-conductive material, and 14a corresponds with dual electrodes of FIGS. 2 and 3. Insulator 20a separates the two electrodes of the device. The device in FIGS. 8 and 9 has an additional electrical connector 74 connected to the external power source, pulse generating and polarity switching device 75. The device 75 is equipped so that pulse frequency, current density and polarity switching period is adjustable.

The cathode and anode of the device of this invention are made of component materials such as silver, copper, molybdenum, stainless steel or other materials that will either (1) be "sacrifical", meaning they will oxidize during operation, or (2) resist corrosion during subsequent operation.

If karaya gum is used for the gel layer, it will be electrochemically conductive and will be more desirable for contact with skin due to high water retention and a natural pH buffer action (pH 4-5).

A karaya gum gel is usually made from approximately 50 parts by weight karaya gum, 25 parts by weight water and 25 parts by weight propylene glycol or glycerin. Due to the high water retentionionic drugs can be added with minimum effect on the gel. The amount of drug added depends on the desired unit dosage per unit time, size of gel layer in contact with active electrode, amount of current used, and other variables.

To the electrode side of the above gel layer is an ion exchange member separating the electrodes and the ionic drug impregnated gel layer for inhibiting the flow of ions of similar charge created by the electrode material. The ion exchange membrane is made of a microporous material and will vary with drug used in the gel layer.

Suitable ion exchange membranes available under the designation AR103-QZ by Ionics, Inc. and Raipore 4010 and 4035 by RAI Research Corp. The outer surface of the ion exchange membrane is affixed with conductive pressure sensitive adhesive for contacting the electrodes of the iontophoretic device. Both surfaces of the gel layer, including the ion exchange membrane, are covered with a release liner for removal when the drug gel layer is used. The final layer is then pouched in a protective pouch to maintain the drug at the desired concentration until use.

Known devices for pulse generating can be used in this invention. One of these devices comprises a pulse generator and a charge pump type voltage converter circuit for increasing the output current of the pulse. By using this type of voltage increasing device to double or triple the voltage of a thin layer battery, it may be possible to achieve the current to overcome the high resistance of the skin (i.e., skin resistance is of the order of 10K ohms to 1M ohms). Also, by pulsing, higher currents can be applied with less irritation, burns, etc. to the skin under the electrodes.

To the known pulse generating device added for purposes of this invention, is a timed electronic reversing circuit to change the anode and the cathode electrodes at a predetermined time period corresponding to a number of pulses. The number of pulses between reversal of the anode and cathode is determined to give a positive drug delivery at the active electrode before reversing the active electrode to the indifferent electrode. It has been determined that higher current densities deliver higher concentrations of ionized drug in less time than lower current densities. Therefore, by pulsing higher current to the active electrode the ionized drug is delivered through the skin faster and goes into the bloodstream faster. This prevents the drug from leaving the skin during reversal of the electrodes. The skin also has a tendency to become polar with the charge being used over long periods of continuous iontophoresis, causing increased resistance to ionized drug delivery. Reversing of the electrodes prevents polarization from occurring, thus minimizing the natural resistance of the skin to ionized drug delivery and increasing the amount of drug delivered over time.

A thin layer battery is used to supply power to the current switching, and or pulse generating devices. Such a battery uses thin layers of a flexible conductive polymer material in sheets layered with a gel substance to generate voltage. By employing the current doubling circuit above, the transdermal drug delivery rate can be increased.

The circuit, including the battery, the pulse generating device and the switch device, is layered to reduce the total thickness to the iontophoretic device. The thickness is kept to from 0.5 millimeters which will allow for a device of no more than 1. to 25. millimeters.

The selection of an outer layer is made to protect the electrical circuits and the two electrodes of the device and provide a cavity for the active ionic gel material containing the drug. Materials such as polyethylene and polypropylene, or any non-conductive polymer that can be molded to the desired shape and that offers protection to the electrode circuit, can be used. However, a polymer that is reasonably flexible so that it bends with the skin is most desirable.

We claim:

1. An iontophoretic device for delivery of a drug comprising:
    a flexible, non-conductive backing layer;
    first and second conductive electrodes in a plane composed of a substantially non-ionizing material, attached to one side of which plane is said backing layer and the other side of which plane is adapted to be affixed to one side of a flexible and electrically conductive layer containing drug to be delivered;
    a source of electrical current;
    means for reversing the polarity of the two electrodes;
    a pulse generator means for delivering current to the electrodes in timed intervals;
    a switch means for reversing the polarity between electrodes during an intermission period of the therapeutic pulse; and
    ion exchange means for separating the electrodes and the conductive layer to inhibit the flow of ions to the electrically conductive layer from the electrode having a charge similar to that of the drug.

2. The device of claim 1, which additionally contains a conductive layer containing the drug to be delivered, affixed to the electrodes.

3. The device of claim 2, wherein the conductive layer is a gel containing a drug in ionic form.

4. The device of claim 1, which additionally contains a conductive layer containing the drug to be delivered, one side of the conductive layer carrying said ion exchange means and the other side attached to the two electrodes.

5. The device of claim 4 in which the conductive layer is a gel.

6. The device of claim 4 in which the drug is contained in karaya gel.

7. An iontophoretic device comprising:
    a flexible, non-conductive backing layer;
    first and second conductive electrodes in a plane having two sides and composed of a substantially non-ionizing material, one side of which is affixed to the flexible backing layer
    a flexible conductive layer containing a drug and affixed to the other side of the electrode;
    a source of electrical current;
    means for reversing the polarity between the two electrodes during operation;
    pulse generator means for delivering current to the electrodes in timed intervals; and
    ion exchange means separating the electrodes and the conductive layer to inhibit the flow of ions to the conductive layer from the electrode having a charge similar to that of the drug.

8. The device of claim 7, wherein the conductive layer is a gel containing an ionic drug.

9. A flexible and electrically conductive material adapted and sized to be affixed to a non-conductive backing layer of an iontophoretic device and comprising a flexible layer of a drug in a conductive material, a pressure sensitive adhesive on both sides of said flexible layer, the pressure sensitive adhesive having sufficient adhesive strength to attach to the skin on one side and to an electrode at the other side and an ion exchange means on one side of the pressure sensitive adhesive intermediate the drug layer and the adhesive.

* * * * *